United States Patent [19]

Jakubowicz et al.

[11] Patent Number: 4,798,705
[45] Date of Patent: Jan. 17, 1989

[54] COMPACT ANALYZER

[75] Inventors: Raymond F. Jakubowicz, Rush; John S. Lercher, Rochester, both of N.Y.

[73] Assignee: Eastman Kodak Company, Rochester, N.Y.

[21] Appl. No.: 13,223

[22] Filed: Feb. 6, 1987

Related U.S. Application Data

[63] Continuation-in-part of Ser. No. 813,286, Dec. 24, 1985, abandoned.

[51] Int. Cl.⁴ .................... G01N 27/26; G01N 21/25
[52] U.S. Cl. ........................ 422/63; 204/403; 422/65; 422/99; 422/104; 422/50
[58] Field of Search ............ 422/50, 63, 64, 65, 422/66, 99, 100, 101, 104; 436/43, 46, 47, 48; 211/1.3; 141/379, 87 R, 380, 381

[56] References Cited

U.S. PATENT DOCUMENTS

| | | | |
|---|---|---|---|
| 1,324,682 | 12/1919 | McIntyre | 141/380 |
| 1,587,676 | 6/1926 | Patterson | 211/1.3 |
| 2,541,438 | 2/1951 | Rossman | 211/1.3 |
| 3,302,452 | 2/1967 | Leslie | 422/65 |
| 3,951,605 | 4/1976 | Natelson | 422/65 |
| 3,992,158 | 11/1976 | Przybylowicz et al. | 422/65 |
| 4,054,415 | 10/1977 | Seligson et al. | 422/64 |
| 4,224,032 | 9/1980 | Glover et al. | 436/46 |
| 4,257,862 | 3/1981 | Schnipelsky et al. | 422/63 |
| 4,287,155 | 9/1981 | Tersteeg et al. | 422/64 |
| 4,303,611 | 12/1981 | Jessop | 422/65 |
| 4,341,736 | 7/1982 | Drbal et al. | 422/64 |
| 4,346,056 | 8/1982 | Sakurada | 422/64 |
| 4,424,191 | 1/1984 | Jakubowicz | 422/65 |

Primary Examiner—Michael S. Marcus
Attorney, Agent, or Firm—Dana M. Schmidt

[57] ABSTRACT

There is disclosed an analyzer comprising a dispensing station and detecting means for detecting either a colorimetric or a potentiometric change in a test element. A pipette support is provided to assist in the liquid dispensing, such support being movably connected to the analyzer to permit the pipette support to be moved from an inoperative position to an operative position, and back.

9 Claims, 8 Drawing Sheets

COMPACT ANALYZER

This is a continuation-in-part of application Ser. No. 813,286 filed Dec. 24, 1985 abandoned.

FIELD OF THE INVENTION

This invention relates generally to an analyzer for detecting quantities of analytes in liquids. More specifically, it relates to such an analyzer constructed to be compact for ease in portability.

BACKGROUND OF THE INVENTION

The trend in the field of dry chemistry blood analysis is towards smaller instruments, for use by smaller institutions and individuals, e.g., doctor's offices. This is evident from the fact that early, commercial dry chemistry analyzers were large machines designed for the large hospital or clinical laboratory, as shown, for example, in U.S. Pat. No. 4,287,155, issued Sept. 1, 1981. (As used herein, "dry chemistry" refers to tests wherein there are no liquid reagents stored for use, such tests having been made possible by test elements of the type described in, e.g., U.S. Pat. No. 3,992,158, issued Nov. 16, 1976.) More recently, the analyzers have been reduced in size, complexity and cost, so as to be useful in doctor's offices, e.g., as shown in U.S. Pat. Nos. 4,303,611 and 4,424,191.

Although such reductions have greatly increased the versatility of the dry chemistry analysis technology, further reduction could provide the additional advantages of portability and use by other than highly skilled doctors and their assistants.

One of the problems that the prior art had not overcome, prior to this invention, concerning portability, is the height of the analyzer necessitated by the presence of the dispensing station used with a pipette. That is, as shown for example in the aforesaid U.S. Pat. No. 4,424,191 the analyzer has included a station for supporting a pipette removably positioned above a test element. A support for the pipette avoids dispensing errors that can occur without a support. The support for such positioning of the pipette has necessitated that the analyzer have considerable height extending above the real working plane of the analyzer, namely, the plane of the test element. Such height makes the analyzer quite bulky, and thus less portable, than it would be without the height required for the dispensing station. Yet, it has not been desirable to do away with the dispensing station since best results are achieved if incubation of the test element occurs immediately, and in a controlled environment, following dispensing with a pipette. That is, a full function analyzer is desired. Such is not readily achieved if dispensing is done on a different apparatus than on the analyzer.

SUMMARY OF THE INVENTION

There is provided an analyzer that overcomes the portability problems of prior art analyzers noted above.

More specifically, there is provided an analyzer including a dispensing station and means for detecting a colorimetric or a potentiometric change in a test element on which a test liquid is dispensed at the dispensing station, the dispensing station including a pipette support for orienting a pipette to dispense such liquid at the dispensing station. The analyzer is improved in that it further includes means for connecting the pipette support to the analyzer, said connecting means being releasible to permit said support to move from an operative position on the analyzer associated with the dispensing station, to a position removed from the operative position, and back, whereby when the pipette support is disengaged, the height of the analyzer is reduced compared to the height when the support is in its operative position.

Accordingly, it is an advantageous feature of the invention that a full function, dry chemistry analyzer is provided that is portable because its total height is reducible when not in use.

It is a related advantageous feature of the invention that such an analyzer provides for both the liquid-dispensing function using a pipette, and compactness when not in use.

Yet another advantageous feature of the invention is that such an analyzer allows the same dual pipette to be used for dispensing liquid onto a colorimetric test element as is used for dispensing liquid onto a potentiometric test element.

Other advantageous features will become apparent upon reference to the discussion of the preferred embodiments, when read in light of the attached drawings.

BRIEF DESCRIPTION OF THE INVENTION

The invention is particularly described in connection with preferred embodiments, wherein both colorimetric and potentiometric test capability are provided, with independent pipette support for each of such tests. Additionally, the preferred embodiment features the testing of biological liquids. In addition, the invention is also applicable to an analyzer having only one of the colorimetric and potentiometric testing capability, or even some other kind of testing capability, so long as a dispensing station is provided. It is also applicable regardless of the type of liquid being tested, particularly since the compactness of the analyzer makes it attractive for field testing of industrial liquids such as waste water, and the like.

Figure 1:
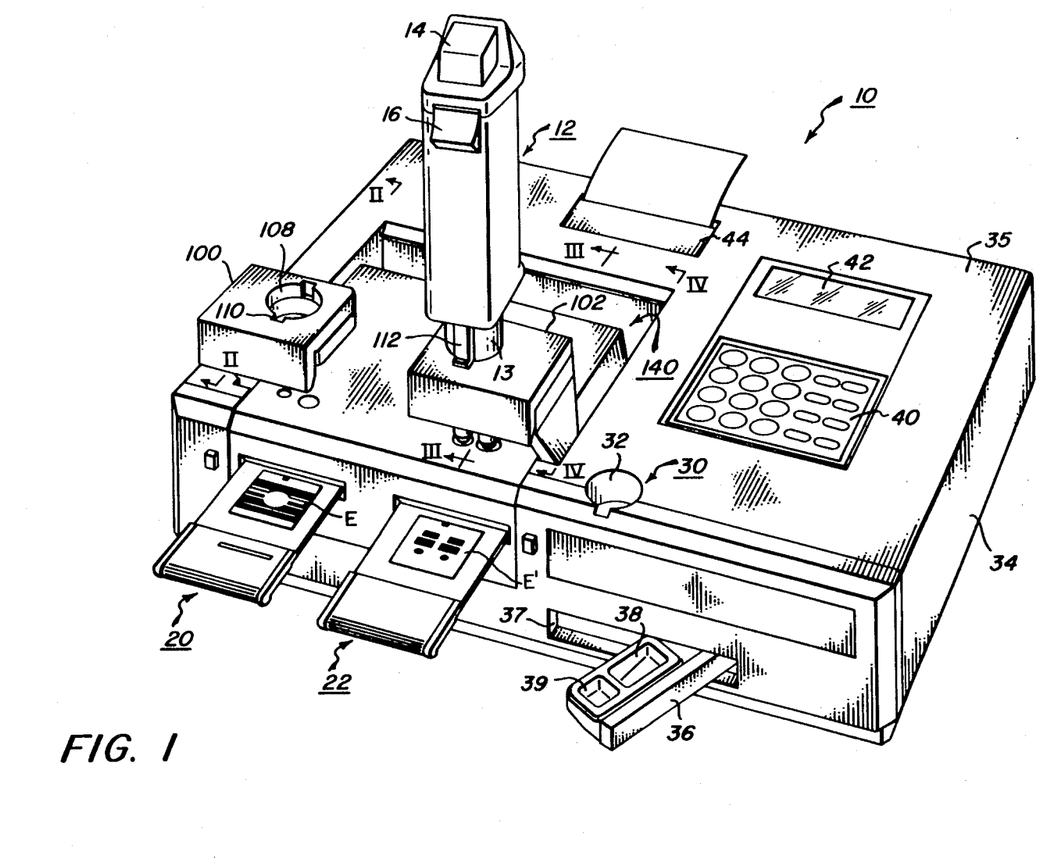
FIG. 1 is an isometric view of an analyzer constructed in accordance with the invention.

As in conventional full-function analyzers, an analyzer 10 constructed in accordance with the invention, FIG. 1, is adapted for use with a pipette 12, and comprises a first movable support 20 for a first test element; a second movable support 22 for a second test element; an aspirating station 30 for loading the pipette with test sample liquid, and optionally, with a reference liquid; an input keyboard 40; a transitory display device 42; and a permanent record display device 44. Keyboard 40 and display devices 42 and 44 are conventional, e.g., device 42 is a 16 character by 4 line liquid crystal display and device 44 is a thermal dot matrix printer.

Any pipette 12 is satisfactory, provided it is dimensioned to fit the pipette support hereinafter described in detail. Preferably it uses disposable tips. Actuating button 14 drives the piston of the pipette, whereas button 16 is used to eject used disposable tips.

Figure 2:
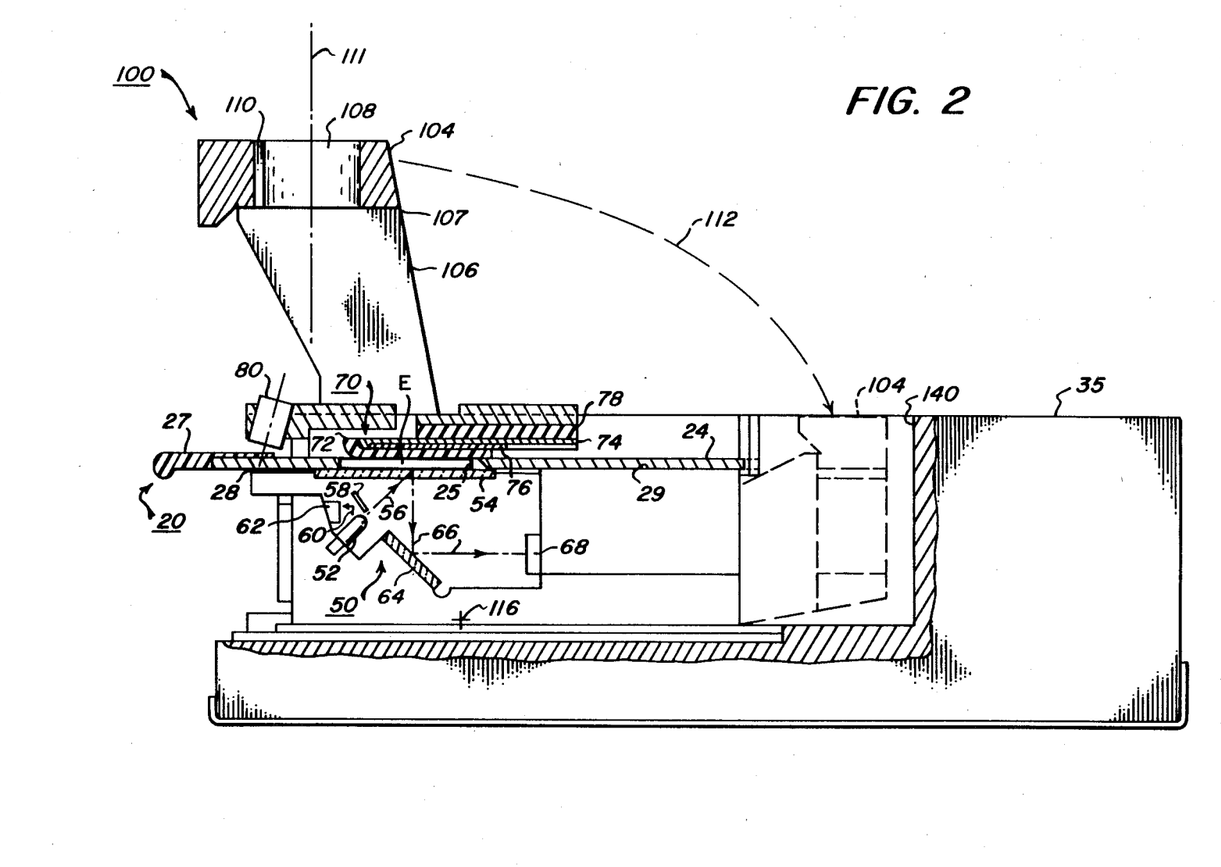
FIG. 2 is an elevational view, partially in section, taken vertically and generally along the plane II—II of FIG. 1.
Figure 3:
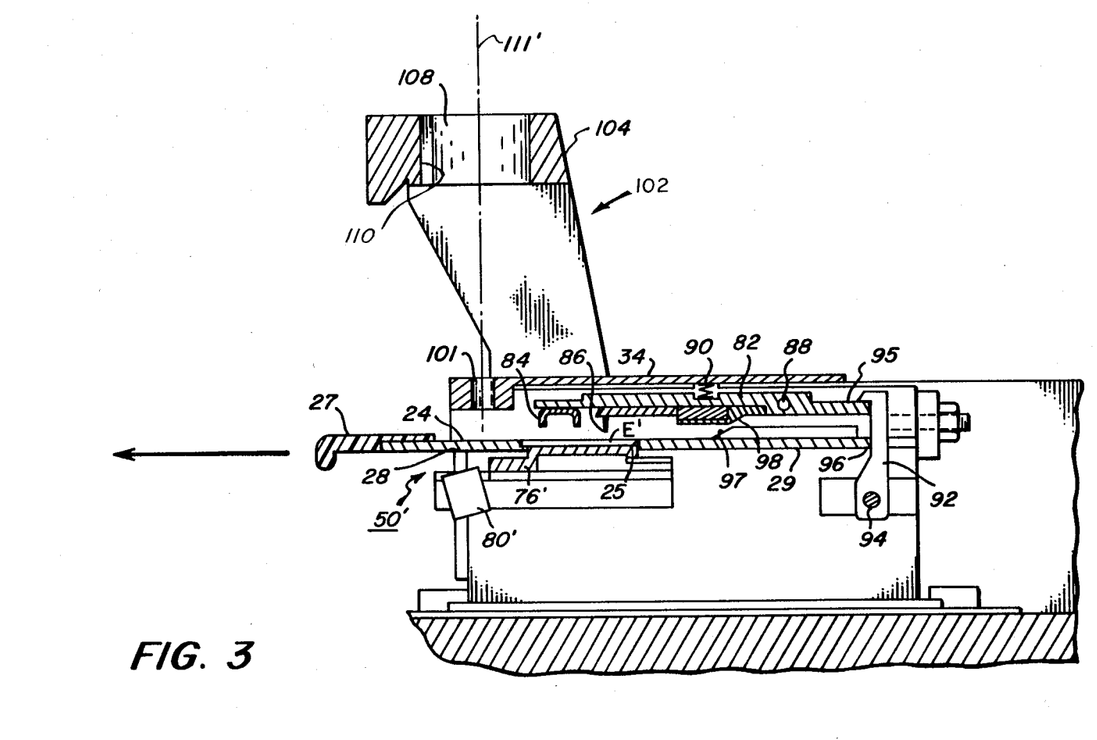
FIG. 3 is a fragmentary section view similar to that of FIG. 2, except taken generally along the vertical plane III—III of FIG. 1.

Supports 20 and 22 each comprise, FIG. 2 and 3, a pusher blade 24 having a pocket 25 that receives one of the test elements E or E'. A handle 27 is provided on the blade for ease in manipulation. The blade reciprocates on surfaces 28, 29. Most preferably, element E is constructed in the manner of the elements described in U.S. Pat. No. 4,258,001, issued on Mar. 24, 1981, or the aforesaid U.S. Pat. No. 3,992,158, e.g., to analyze for glucose.

Aspirating station 30, FIG. 1, comprises a pipette mount aperture 32 in the frame 34 of the analyzer, and a pivotable support arm 36 mounted in opening 37, to hold a tray having two wells 38 and 39. Well 38 is loaded with the sample liquid to be analyzed and well 39 is loaded with a reference fluid when a potentiometric measurement is to be made. Aperture 32 extends all the way to opening 37.

Frame 34 provides an overall top surface 35 of the analyzer which is reduced in height. That is, the overall height of the analyzer, not counting supports 100 and 102 when in use as described below, can be as little as 8 cm.

Read stations 50 and 50' are provided for detecting the reaction that takes place in each of elements E and E'. Station 50, FIG. 2, is a colorimetric detection station, comprising a reflectometer for detecting reflection densities. The details of the reflectometer are conventional, and can be adapted from a variety of techniques. Preferably, at least one LED 52 is disposed to illuminate element E through a transparent member 54, along arrow 56. A small mirror 58 is positioned to reflect a sideways-directed portion of the LED light, arrow 60, to a reference detector 62. A larger mirror 64 is used to reflect, via arrows 66, diffusely reflected radiation from element E to detector 68.

A hold-down pad 70 preferably is used to bias element E against transparent member 54. Pad 70 comprises a non-scratching, non-absorbent cover 72, comprising, for example, Teflon TM coated aluminum, mounted on frame 74, and a conventional heating element 76. Frame 74 is backed up by a resilient layer 78 that allows pad 70 to move vertically when an element E is pushed into place for detection. Pad 70 also serves to prevent evaporation and/or gas leakage from element E.

Figure 5:
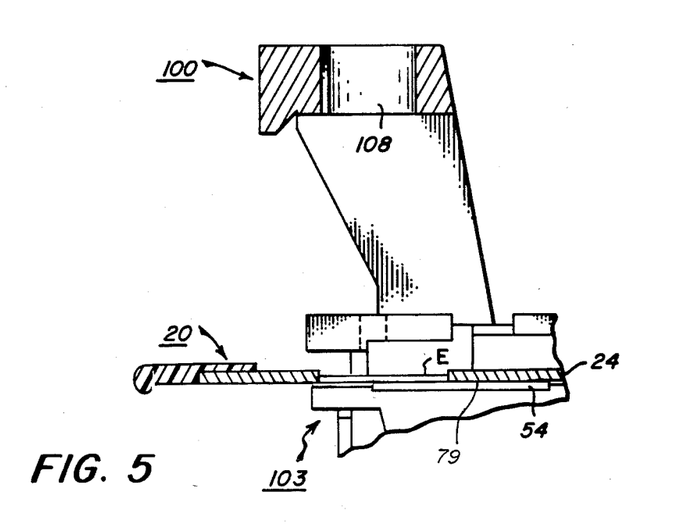
FIG. 5 is a fragmentary sectional view similar to that of FIG. 2.

A white reference surface 79, FIG. 5, on pusher blade 24 allows the system to take reference optical measurements when the element is in the metering station.

Optionally, a conventional bar code reader 80 is included above blade 24.

Read station 50', FIG. 3, is used to detect changes in element E' created by ionic analytes. Most preferably, element E' is constructed in the manner described in U.S. Pat. No. 4,053,381, issued on Oct. 11, 1977, and U.S. Pat No. 4,214,968, issued on July 29, 1980.

Station 50' preferably comprises a heater platen 76' and a vertically movable arm 82 that mounts a cover 84 and electrode contacts 86. The cover is designed to fit over the spotting holes of element E' to prevent evaporation. Both cover 84 and contacts 86 raise and lower in response to the pivoting of arm 82 about pivot point 88. Arm 82 is biased downwardly by spring 90, and latch 92 is provided to hold arm 82 with cover and contacts raised, when element E' is moved in and out of position. That is, latch 92 pivots at 94 to clamp onto end 95 of arm 82, except when end 96 of blade 24 pushes against the latch on the completion of its inward stroke. A cam shoulder 97 is mounted on blade end 96 to cooperate with cam follower 98 hanging from arm 82. That is, when blade 24 starts its return stroke to pull out element E' after reading, cam shoulder 97 forces arm 82 to rotate clockwise until it again latches with latch 92.

Conventional circuitry, not shown, carries signals from contacts 86 to the rest of the analyzer.

Optionally, a bar code reader 80' is disposed below blade 24 at station 50', to read bar codes on the underneath surface of element E'.

As best shown in FIG. 3, frame 34 is provided at each station 50 and 50' with pairs of apertures 101 aligned with aperture 108, to accommodate the twin disposable tips of the pipette when the latter is mounted in the pipette support.

All the signals generated by the analyzer are processed by a conventional microprocessor, not shown, using conventional programming. The input from the keyboard 40, as well as the output on the displays, are received and directed, respectively, by such microprocessor, as is conventional.

In accordance with one aspect of the invention, pipette supports 100, 102 are movably or releasible connected to frame 34, so that they are movable into and out of an operative position, shown in FIG. 2, associated with dispensing station 103, FIG. 5. When disengaged from such operative position, they can be moved into, respectively, an inoperative withdrawn position, shown in phantom in FIG. 2. Such supports comprise, FIGS. 2-4, a yoke 104 connected to the frame via an arm 106. Each yoke is fixed to one end 107 of arm 106 and is provided with a pipette mounting aperture 108. Aperture 108 is configured to accommodate the dispensing end of pipette 12 up to collar 13 of the pipette, FIG. 1. A keyway 110 is preferably formed in aperture 108 to cooperate with key ridge 112 formed in collar 13, to insure the pipette is properly angularly positioned about an axis 111 or 111', FIGS. 2 and 3.

Figure 4:
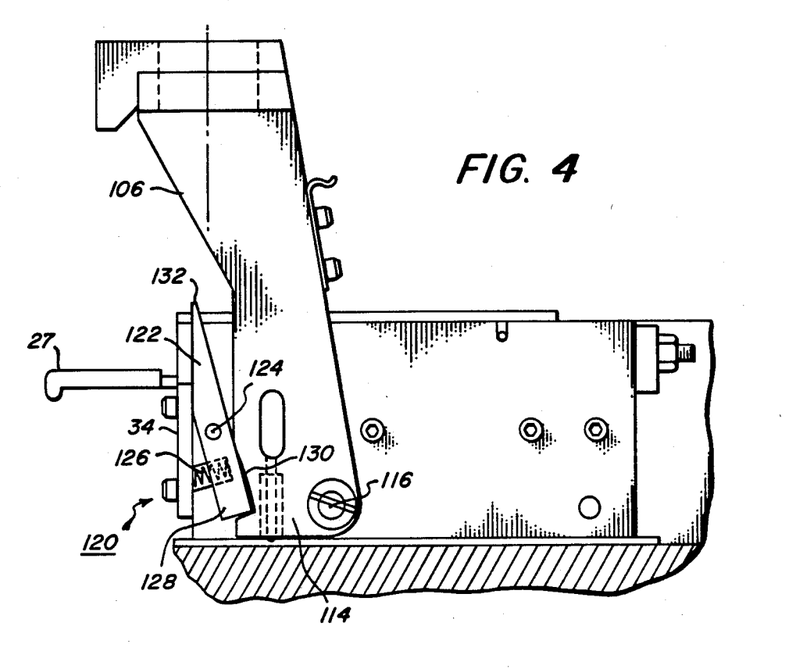
FIG. 4 is a fragmentary sectional view taken generally along the plane IV—IV of FIG. 1.

The opposite end 114, FIG. 4, of arm 106 is journalled to frame 34 on axis 116 to allow the arm to rotate between the operative position shown in solid lines, FIGS. 2-4, and the withdrawn position shown in dashed lines of FIG. 2.

The two supports 100 and 102 are mirror images of each other, except as follows: Support 100 is constructed to assist in the dispensing of liquid onto a colorimetric element E' FIG. 2, whereas support 102 is constructed to assist in the dispensing of liquid onto a potentiometric test element E', FIGS. 3 and 4. In addition, to allow the same dual pipette 12 (having twin disposable tips) to be used for either element E or E', aperture 108 in support 100 preferably is displaced sideways a sufficient distance from the centerline of element E, so as to ensure that only the disposable tip containing sample liquid, lines up with the test element. (The dispensing position of element E in dispensing station 103, relative to support 100, is shown in FIG. 5, wherein blade 24 is pulled farther out of the analyzer than in FIG. 2.)

Optionally, a portion of yoke 104 can include a conventional sensor (not shown) to sense the movement of the pipette piston that is indicative of a dispensing event. Examples of such a sensor include a reed switch and a Hall effect switch.

To hold the pipette supports preferably in their upright, operative positions, a latch 120 is provided, FIG. 4, for the arms of each support. The latch comprises a lever 122 journalled at 124 to frame 34, and a spring 126 biasing end 128 of the latch so as to snap end 128 into end 114 of arm 106 at a notch 130. When the opposite end 132 of lever 122 is pushed against the bias of spring 126, latch 120 releases from arm 106, and the support can be rotated down, arrow 122, FIG. 2, into its withdrawn position.

Figure 6:
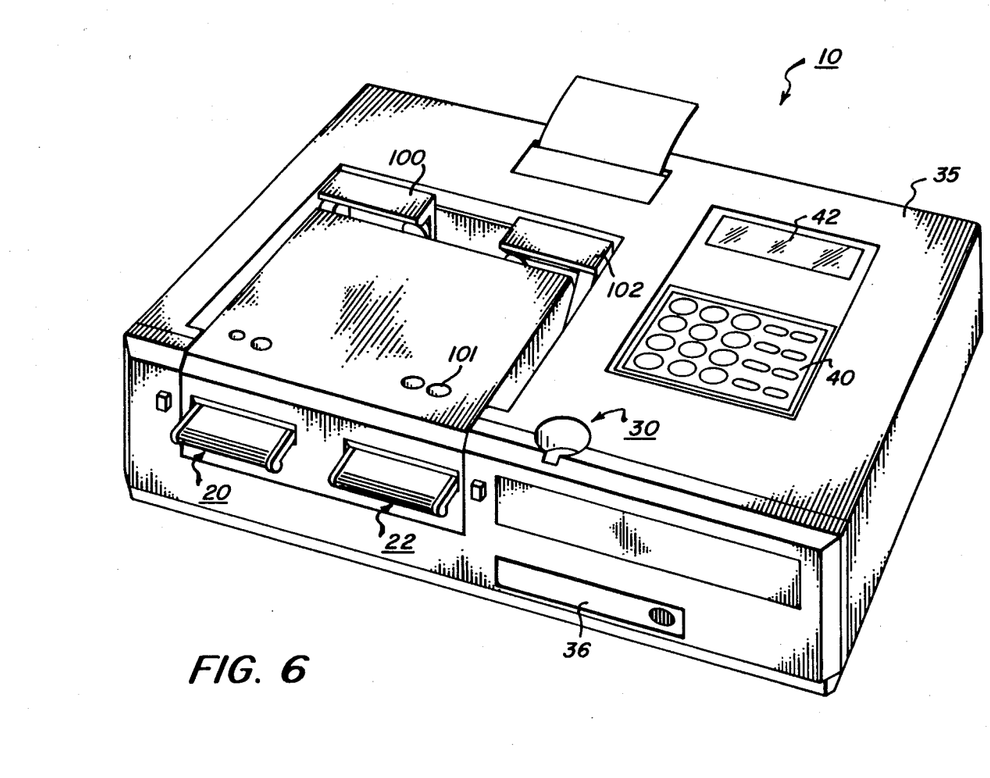
FIG. 6 is a isometric view similar to that of FIG. 1, except with the pipette supports in their withdrawn positions.

Preferably, a cavity 140 is provided in frame 34 of the analyzer, FIG. 1. Cavity 140 has sufficient depth to store the entire yoke 104 of each support 100 and 102, so that the yokes do not project above top surface 35 of the analyzer, FIGS. 2 and 6. Thus, when the analyzer is not in use, it is very compact and readily portable.

Figure 7:
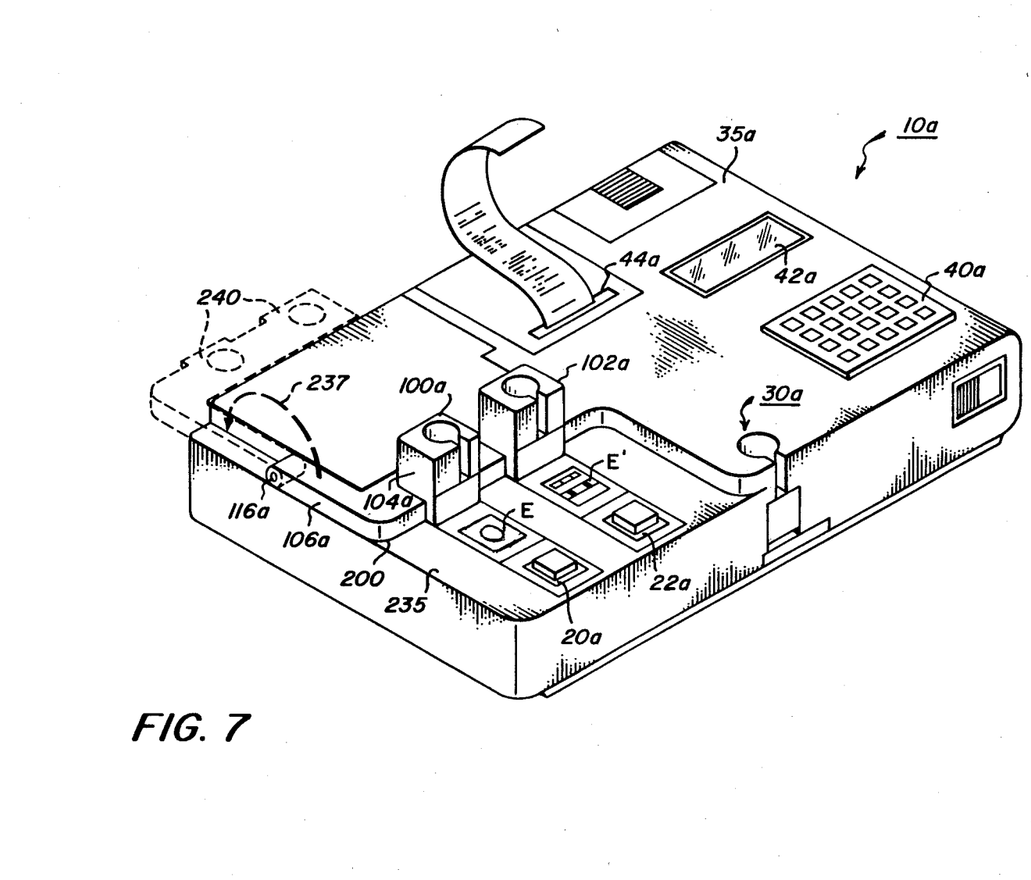
FIG. 7 is an isometric view of another embodiment of the invention

It is not necessary that supports 100 and 102 be separately mounted on individual arms 106. Alternatively, as shown in FIG. 7, they can be mounted on a single arm. Parts similar to those previously described have the same reference numeral, to which the distinguishing suffix "a" is appended.

Thus, analyzer 10a includes, as in the previous embodiment, movable supports 20a and 22a for colorimetric and potentiometric, respectively, test elements E and E'. Aspirating station 30a functions as before, as do keyboard 40a and display devices 42a and 44a. Also, yokes 104a of pipette supports 100a and 102a function as before to provide support during dispensing of liquid from the pipette shown in the previous embodiment.

Unlike the previous embodiment, yokes 104a are mounted on a single arm 106a that swings about a pivot point 116a. Underneath surface 200 of arm 106a abuts against surface 235 of analyzer 10a so as to hold yokes 104a spaced above the analyzer, permitting elements E and E' to slide into place for dispensing. When the analyzer is to be stored or carried, arm 106a is rotated, arrow 237, out of its solid line position and into the dotted line storage position, so that the bottom surfaces 240 of yokes 104a are at or below the top surface 35a of the analyzer the extension of cut-away surface 235 towards the back of the analyzer provides the storage compartment.

It is further unnecessary that the pipette supports be attached to the remainder of the analyzer on a permanent basis, or indeed that they be stored within the analyzer. In yet another alternative, FIGS. 8 and 9, the supports are removably secured in an operative position, and after use are disengaged entirely for storage within the analyzer, at the side of the analyzer, or at a location totally unassociated therewith. Parts similar to those previously described have the same reference numeral, to which the distinguishing suffix "b" is appended.

Figure 8:
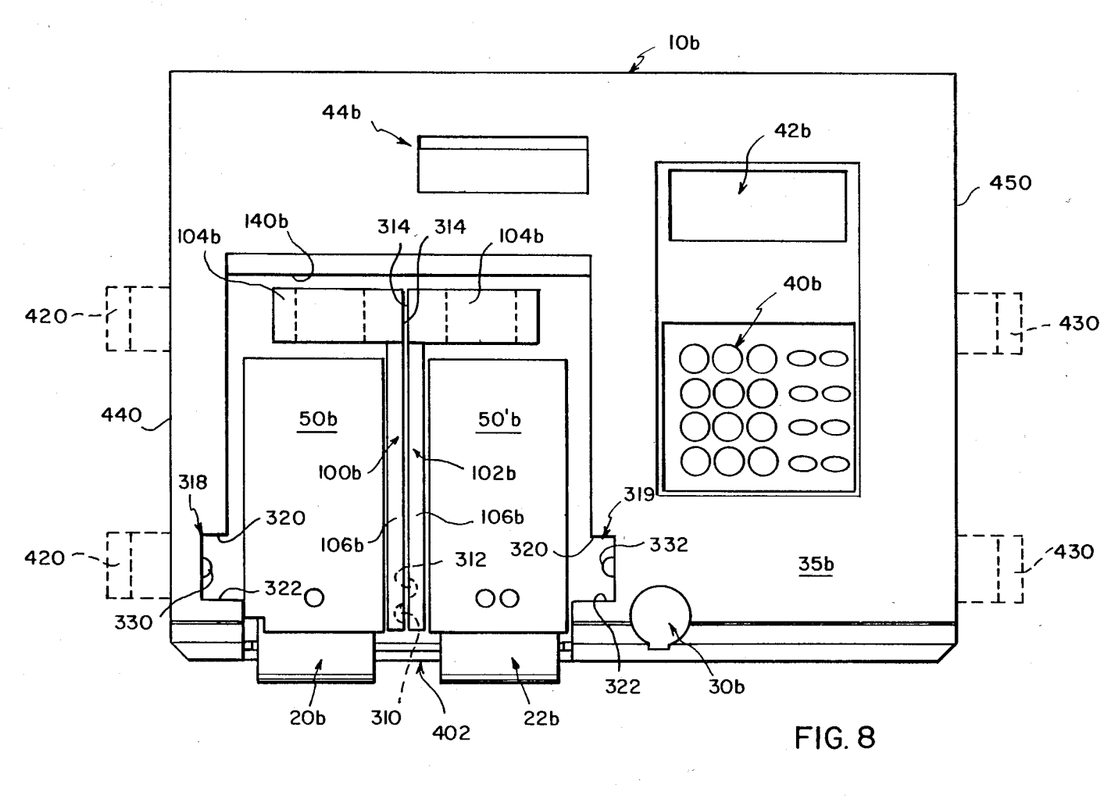
FIG. 8 is a plan view of yet another embodiment of the invention, with some parts removed.

Thus, FIG. 8, the analyzer 10b comprises, as before, supports 20b and 22b for moving the test elements into and out of position, aspirating station 30b, keyboard 40b and display devices 42b and 44b. Pipette supports 100b and 102b are also provided to function in their operative positions exactly as the embodiment shown in FIG. 1 functions, as described above.

Figure 9:
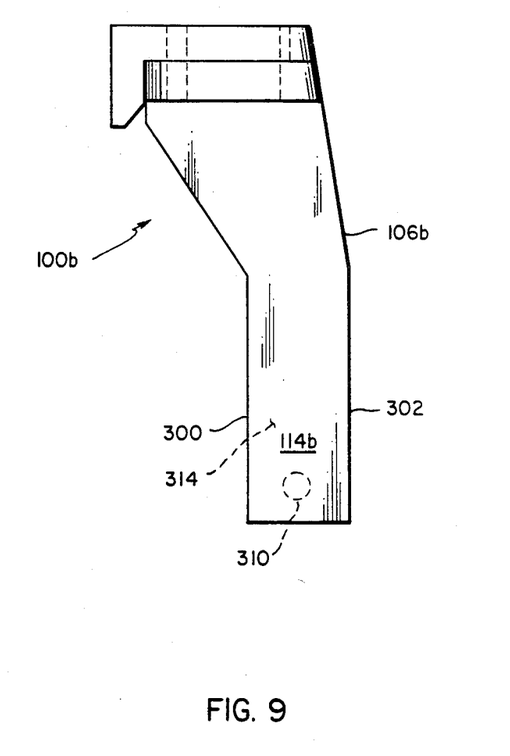
FIG. 9 is a side elevational view of one of the pipette supports used in the embodiment of FIG. 8.

Unlike the previous embodiments, however, supports 100b and 102b are totally disengageable from the rest of the analyzer for storage when not in use. Arms 106b are modified for this purpose, as shown in FIGS. 8 and 9. That is, end 114b is provided with generally parallel opposed edges 300, 302, and a semi-spherical indentation 310 or 312 in the outside surface 314. Indentation 312 is at a location slightly higher than indentation 310, so that there is no opportunity to mount a pipette support within the wrong slot, described hereinafter.

These features of the supports have corresponding mating features in the analyzer as follows:

Vertical grooves 318 & 319 are formed with side walls 320, 322 that accommodate the width of arm 106b measured between edges 300, 302. A spring biased ball detent 330 or 332 is provided at the appropriate height from the bottom of grooves 318 and 319, to releasibly engage indentations 310 and 312, respectively, in the arm ends 114b of supports 100b and 102b.

Additionally, FIG. 8 illustrates the manner in which supports 100b and 102b can be optionally stored when not in use. When the cover, shown in FIG. 6 with aperture 101, is removed, the individual read stations 50b and 50'b appear. There is sufficient space between them, shown at 402, to accommodate arms 106b of both supports. Additionally, there is the space between stations 50b and 50'b, and wall 140b, which space is shown also in FIG. 2, to accommodate yokes 104b, so that the supports are stored recessed within the analyzer when not in use.

Alternatively, however, the removed supports 100b and 102b can be mounted on clips 420 and 430, respectively, that extend from the sides 440 and 450 of the analyzer, still without extending above the height of surface 35b of the analyzer. Furthermore, it will be readily apparent that they can be stored at a location disassociated with the analyzer, for example, with the pipette.

The invention has been described in detail with particular reference to preferred embodiments thereof, but it will be understood that variations and modifications can be effected within the spirit and scope of the invention.

What is claimed is:

1. In an analyzer including a dispensing station and means for detecting a colorimetric or a potentiometric change in a test element on which a test liquid is dispensed at said dispensing station, said dispensing station including a pipette support for orienting a pipette to dispense the liquid at said dispensing station, said analyzer having an overall top surface;

the improvement wherein said analyzer further includes means for movingly connecting said pipette support to the analyzer to permit said support to move into and out of an operative position on said analyzer associated with said dispensing station, and out of and into, respectively, a withdrawn position in said analyzer, removed from said dispensing station;

and wherein said withdrawn support position is at or below said top surface, and said operative pipette support position is above said top surface, so that when said pipette support is moved into the analyzer, the height of said analyzer is reduced compared to said height when said support is in said operative position.

2. An analyzer as defined in claim 1, wherein said pipette support comprises (a) a yoke having an aperture constructed to accommodate therethrough a dispensing end of a pipette, (b) a linking arm having two ends, one of which is affixed to said yoke, the other end of said arm being rotatably connected to the analyzer for rotation of said arm between said withdrawn position and said operative position, and (c) a latch for latching said arm in said operative position of said pipette support.

3. An analyzer as defined in claim 1, further including, adjacent said dispensing station, an additional dispensing station, and an additional pipette support for orienting a pipette mounted therein to dispense liquid at said additional dispensing station, and means for movingly connecting said additional pipette support to the analyzer to permit said additional support to move in an out of an operative position associated with said additional dispensing station, and out of and into, respectively, a withdrawn position for said additional support that is removed from said additional dispensing station, said withdrawn position of said additional pipette support being located so that when said additional pipette support is moved thereinto, the height of said analyzer is reduced compared to said height when said additional pipette support is in its operative position.

4. An analyzer as defined in claim 3, wherein one of said dispensing stations includes means permitting metering of a liquid from a pipette mounted in its respective one of said pipette supports, onto a colorimetric test element located in one of said dispensing stations, and the other of said dispensing stations includes means permitting metering onto a potentiometric test element located in the other of said dispensing stations.

5. An analyzer as defined in claim 4, wherein each said pipette support comprises a yoke having an aperture constructed to accommodate therethrough the dispensing end of a pipette, and an arm rotatably connected to the analyzer, and wherein said yoke apertures are positioned within said yokes to allow the same pipette to be used to dispense liquid at each of said dispensing stations.

6. In an analyzer including a dispensing station and means for detecting a colorimetric or a potentiometric change in a test element on which a test liquid is dispensed at said dispensing station, said dispensing station including a pipette support for orienting a pipette to dispense the liquid at said dispensing station, said analyzer having an overall top surface;

the improvement wherein said analyzer further includes means for connecting said pipette support to the analyzer, and a storage compartment recessed below said top surface, said connecting means being releasable to permit said support to move from an operative position on said analyzer associated with said dispensing station, to said storage compartment, and back, whereby when said pipette support is released and in said storage compartment, the height of said analyzer is reduced compared to said height when said support is in said operative position.

7. An analyzer as defined in claim 6, wherein said connecting means is constructed to permit complete disengagement and disassociation of said pipette support from said analyzer.

8. An analyzer as defined in claim 6, further including, adjacent said dispensing station, an additional dispensing station, and an additional pipette support for orienting a pipette mounted therein to dispense a test liquid at said additional dispensing station, and means for releasibly connecting said additional pipette support to the analyzer in an operative position on said analyzer associated with said additional dispensing station, said connecting means permitting movement of said additional pipette support to a withdrawn position removed from said operative position, and back, whereby when said additional pipette support is withdrawn the height of said analyzer is reduced compared to said height when said additional support is in its operative position.

9. An analyzer as defined in claim 8, wherein one of said dispensing stations includes means permitting metering onto a colorimetric test element, and the other of said dispensing stations includes means permitting metering onto a potentiometric test element.

* * * * *

UNITED STATES PATENT AND TRADEMARK OFFICE
CERTIFICATE OF CORRECTION

PATENT NO.   : 4,798,705

DATED        : January 17, 1989

INVENTOR(S)  : Jakubowicz, Raymond F. & Lercher, John S.

It is certified that error appears in the above-identified patent and that said Letters Patent is hereby corrected as shown below:

Col. 7, line 14 should read:
--analyzer to permit said additional support to move in and--

Signed and Sealed this

Twenty-first Day of November, 1989

Attest:

JEFFREY M. SAMUELS

Attesting Officer     Acting Commissioner of Patents and Trademarks